(12) United States Patent
Farwick et al.

(10) Patent No.: US 6,924,134 B2
(45) Date of Patent: Aug. 2, 2005

(54) NUCLEOTIDE SEQUENCES WHICH CODE FOR THE GORA GENE

(75) Inventors: Mike Farwick, Bielefeld (DE); Klaus Huthmacher, Gelnhausen (DE); Walter Pfefferle, Halle (Westf.) (DE); Achim Marx, Bielefeld (DE)

(73) Assignee: Degussa AG, Dusseldorf (DE)

( * ) Notice: Subject to any disclaimer, the term of this patent is extended or adjusted under 35 U.S.C. 154(b) by 63 days.

(21) Appl. No.: 09/946,764

(22) Filed: Sep. 6, 2001

(65) Prior Publication Data

US 2002/0106758 A1 Aug. 8, 2002

(30) Foreign Application Priority Data

Sep. 12, 2000 (DE) .......................... 100 44 946
Feb. 24, 2001 (DE) .......................... 101 09 023

(51) Int. Cl.$^7$ .......................... C12N 9/02; C12N 1/20; C12N 15/00; C07K 1/00; C07H 21/04
(52) U.S. Cl. .................. 435/189; 435/69.1; 435/183; 435/252.3; 435/252.32; 435/320.1; 530/350; 536/23.2
(58) Field of Search .................. 435/69.1, 183, 435/189, 252.3, 252.32, 320.1, 252.33; 530/350; 536/23.2

(56) References Cited

U.S. PATENT DOCUMENTS 6,027,920 A * 2/2000 Joliff et al. .................. 435/69.7
2002/0197605 A1 * 12/2002 Nakagawa et al.

FOREIGN PATENT DOCUMENTS

| DE | 199 53 809 | 5/2001 |
| EP | 0 551 614 | 7/1993 |
| EP | 0 733 712 | 9/1996 |
| EP | 0 754 756 | 1/1997 |
| EP | 0 771 879 | 5/1997 |
| EP | 0 854 189 | 7/1998 |
| EP | 1 108 790 A2 | 6/2001 |

OTHER PUBLICATIONS

Attwood et al. Which craft is best in bioinformatics? Comput. Chem. 2001, vol. 25(4), pp. 329–339.*
Ponting, C.P. Issues in predicting protein function from sequence. Brief. Bioinform. Mar. 2001, vol. 2(1), pp. 19–29.*
Song et al. GenBank Accession U97041. (Alignment No. 1).*
Song et al. GenBank Accession U97041. (Alignment No. 2).*
EPO Search Report of PCT/EP01/093140 dated Mar. 11, 2002.
Database EMBL 'Online! Accession No. AF002193, Jun. 28, 1997 XP002190159 *sequence*.
Kramer R "Genetic and Physiological Approaches for the Production of Amino Acids" Journal of Biotechnology, Elsevier Science Publishers, Amsterdam, NL, vol. 45, No. 1, Feb. 12, 1996, pp. 1–21, XP004036833 ISSN: 0168–1656 *abstract, p. 2:1–6:3112:25–16:48, fig. 1, 2, 3, 4,5.
Vallino J J et al: "Carbon Flux Distribution at the Glucose 6–Phosphate Branck Point in Corynebacterium Glutamicum During Lysine Overproduction" Biotechnology Progress, xx, xx, vol. 10, 1994, pp. 327–334, XP000960466 ISSN: 8756–7938 * abstract, p. 329, 334*.
Eggeling L et al., "Improved L–Lysine Yield with Corynebacterium Glutamicum: Use of DAPA Resulting in Increased Flux Combined with Growth Limitation" Applied Microbiology and Biotechnology, Springer Verlag, Berlin, DE, vol. 49, No. 1, 1998, pp. 24–30, XP000918549 ISSN: 0175–7598 *abstract, fig. 1, discussion*.
Hua Qiang et al., "Metabolic Control Analysis for Lysine Synthesis Using Corynebacterium Glutamicum and Experimental Verification", Journal of Bioscience and Bioengineering, vol., 90, No. 2, Aug. 2000, pp. 184–192, XP001055403 ISSN: 1389–1723, * abstract, pp. 189–190*.
An Gil–Hwan et al., "Redirection of Carbon Flux to Lysine in a Recombinant of Corynebacterium Lactofermentum ATCC 21799 by Limited Supply of Pantothenate" Journal of Bioscience and Bioengineering vol. 88, No. 2, Aug. 1999, pp. 168–172, XP001055488 ISSN: 1389–1723, abstract, pp. 168, 171.

* cited by examiner

Primary Examiner—Manjunath N. Rao
Assistant Examiner—Christian L. Fronda
(74) Attorney, Agent, or Firm—Smith, Gambrell & Russell (57) ABSTRACT

The invention relates to an isolated polynucleotide having a polynucleotide sequence which codes for the gorA gene, and a host-vector system having a coryneform host bacterium in which the gorA gene is present in attenuated form and a vector which carries at least the gorA gene according to SEQ ID No 1, and the use of polynucleotides which comprise the sequences according to the invention as hybridization probes.

18 Claims, 1 Drawing Sheet

Figure 1: Plasmid pCR2.1gorAint

NUCLEOTIDE SEQUENCES WHICH CODE FOR THE GORA GENE

BACKGROUND OF THE INVENTION

The invention provides nucleotide sequences from coryneform bacteria which code for the gorA gene and a process for the fermentative preparation of amino acids using bacteria in which the gorA gene is attenuated. All references cited herein are expressly incorporated by reference. Incorporation by reference is also designated by the term "I.B.R." following any citation.

L-Amino acids, in particular L-lysine, are used in human medicine and in the pharmaceuticals industry, in the foodstuffs industry and very particularly in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce amino acids are obtained in this manner.

Methods of the recombinant DNA technique have also been employed for some years for improving the strain of *Corynebacterium* strains which produce L-amino acid, by amplifying individual amino acid biosynthesis genes and investigating the effect on the amino acid production.

The invention provides new measures for improved fermentative preparation of amino acids.

BRIEF SUMMARY OF THE INVENTION

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine is particularly preferred.

When L-lysine or lysine are mentioned in the following, not only the bases but also the salts, such as e.g. lysine monohydrochloride or lysine sulfate, are meant by this.

The invention provides an isolated polynucleotide from coryneform bacteria, comprising a polynucleotide sequence which codes for the gorA gene, chosen from the group consisting of a) polynucleotide which is identical to the extent of at least 70% to a polynucleotide which codes for a polypeptide which comprises the amino acid sequence of SEQ ID No. 2, b) polynucleotide which codes for a polypeptide which comprises an amino acid sequence which is identical to the extent of at least 70% to the amino acid sequence of SEQ ID No. 2, c) polynucleotide which is complementary to the polynucleotides of a) or b), and d) polynucleotide comprising at least 15 successive nucleotides of the polynucleotide sequence of a), b) or c), the polypeptide preferably having the activity of glutathione reductase.

The invention also provides the above-mentioned polynucleotide, this preferably being a DNA which is capable of replication, comprising:
(i) the nucleotide sequence, shown in SEQ ID No.1, or
(ii) at least one sequence which corresponds to sequence (i) within the range of the degeneration of the genetic code, or
(iii) at least one sequence which hybridizes with the sequences complementary to sequences (i) or (ii), and optionally
(iv) sense mutations of neutral function in (i).

The invention also provides:
a polynucleotide, in particular DNA, which is capable of replication and comprises the nucleotide sequence as shown in SEQ ID No.1;
a polynucleotide which codes for a polypeptide which comprises the amino acid sequence as shown in SEQ ID No. 2;
a vector containing parts of the polynucleotide according to the invention, but at least 15 successive nucleotides of the sequence claimed,
and coryneform bacteria in which the gorA gene is attenuated, in particular by an insertion or deletion.

The invention also provides polynucleotides, which substantially comprise a polynucleotide sequence, which are obtainable by screening by means of hybridization of a corresponding gene library of a coryneform bacterium, which comprises the complete gene or parts thereof, with a probe which comprises the sequence of the polynucleotide according to the invention according to SEQ ID No.1 or a fragment thereof, and isolation of the polynucleotide sequence mentioned.

BRIEF DESCRIPTION OF THE FIGURE

The abbreviations and designations used have the following meaning.
KmR: Kanamycin resistance gene
EcoRI: Cleavage site of the restriction enzyme EcoRI
HindIII: Cleavage site of the restriction enzyme HindIII
SacI: Cleavage site of the restriction enzyme SacI
GorAint: Internal fragment of the gorA gene
ColE1: Replication origin of the plasmid ColE1

DETAILED DESCRIPTION OF THE INVENTION

Polynucleotides which comprise the sequences according to the invention are suitable as hybridization probes for RNA, cDNA and DNA, in order to isolate, in the full length, nucleic acids or polynucleotides or genes which code for glutathione reductase or to isolate those nucleic acids or polynucleotides or genes which have a high similarity with the sequence of the gorA gene. They are also suitable for incorporation into so-called "arrays", "micro arrays" or "DNA chips" in order to detect and determine the corresponding polynucleotides.

Polynucleotides which comprise the sequences according to the invention are furthermore suitable as primers with the aid of which DNA of genes which code for glutathione reductase can be prepared by the polymerase chain reaction (PCR).

Such oligonucleotides which serve as probes or primers comprise at least 25, 26, 27, 28, 29 or 30, preferably at least 20, 21, 22, 23 or 24, very particularly preferably at least 15, 16, 17, 18 or 19 successive nucleotides. Oligonucleotides with a length of at least 31, 32, 33, 34, 35, 36, 37, 38, 39 or 40, or at least 41, 42, 43, 44, 45, 46, 47, 48, 49 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70% to 80%, preferably at least 81% to 85%, particularly preferably at least 86% to 90%, and very particularly preferably at least 91%, 93%, 95%, 97% or 99% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of glutathione reductase, and also those which are at least 70% to 80%, preferably at least 81% to 85%, particularly preferably at least 86% to 90%, and very particularly preferably at least 91%, 93%, 95%, 97% or 99% identical to the polypeptide according to SEQ ID No. 2 and have the activity mentioned.

The invention furthermore relates to a process for the fermentative preparation of amino acids chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using coryneform bacteria which in particular already produce amino acids and in which the nucleotide sequences which code for the gorA gene are attenuated, in particular eliminated or expressed at a low level.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

The microorganisms provided by the present invention can prepare amino acids from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 and L-amino acid-producing mutants or strains prepared therefrom.

The new gorA gene from *C. glutamicum* which codes for the enzyme glutathione reductase (EC 1.6.4.2) has been isolated.

To isolate the gorA gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie Verlag Chemie, Weinheim, Germany, 1990) I.B.R., or the handbook by Sambrook et al.: Molecular Cloning, A Laboratory Manual (Cold Spring Harbor Laboratory Press, 1989) I.B.R. may be mentioned as an example. A well-known gene library is that of the *E. coli* K-12 strain W3110 set up in λ vectors by Kohara et al. (Cell 50, 495–508 (1987)) I.B.R. Bathe et al. (Molecular and General Genetics, 252:255–265, 1996) I.B.R. describe a gene library of *C. glutamicum* ATCC13032, which was set up with the aid of the cosmid vector SuperCos I (Wahl et al., 1987, Proceedings of the National Academy of Sciences USA, 84:2160–2164 I.B.R.) in the *E. coli* K-12 strain NM554 (Raleigh et al., 1988, Nucleic Acids Research 16:1563–1575 I.B.R.).

Börmann et al. (Molecular Microbiology 6(3), 317–326)) (1992)) I.B.R. in turn describe a gene library of *C. glutamicum* ATCC13032 using the cosmid pHC79 (Hohn and Collins, 1980, Gene 11, 291–298 I.B.R.).

To prepare a gene library of *C. glutamicum* in *E. coli* it is also possible to use plasmids such as pBR322 (Bolivar, 1979, Life Sciences, 25, 807–818 I.B.R.) or pUC9 (Vieira et al., 1982, Gene, 19:259–268 I.B.R.). Suitable hosts are, in particular, those *E. coli* strains which are restriction- and recombination-defective, such as, for example, the strain DH5αmcr, which has been described by Grant et al. (Proceedings of the National Academy of Sciences USA, 87 (1990) 4645–4649) I.B.R. The long DNA fragments cloned with the aid of cosmids or other λ vectors can then in turn be subcloned and subsequently sequenced in the usual vectors which are suitable for DNA sequencing, such as is described e.g. by Sanger et al. (Proceedings of the National Academy of Sciences of the United States of America, 74:5463–5467, 1977) I.B.R.

The resulting DNA sequences can then be investigated with known algorithms or sequence analysis programs, such as e.g. that of Staden (Nucleic Acids Research 14, 217–232 (1986) I.B.R., that of Marck (Nucleic Acids Research 16, 1829–1836 (1988)) I.B.R. or the GCG program of Butler (Methods of Biochemical Analysis 39, 74–97 (1998)) I.B.R.

The new DNA sequence of *C. glutamicum* which codes for the gorA gene and which, as SEQ ID No. 1, is a constituent of the present invention has been found. The amino acid sequence of the corresponding protein has furthermore been derived from the present DNA sequence by the methods described above. The resulting amino acid sequence of the gorA gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)) I.B.R., in O'Regan et al. (Gene 77:237–251 (1989)) I.B.R., in Sahin-Toth et al. (Protein Sciences 3:240–247 (1994)) I.B.R., in Hochuli et al. (Bio/Technology 6:1321–1325 (1988)) I.B.R. and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) I.B.R. and in Liebl et al. (International Journal of Systematic Bacteriology 41: 255–260 (1991)) I.B.R. The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996 I.B.R.).

A 5×SSC buffer at a temperature of approx. 50° C.–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995 I.B.R.) a temperature of approx. 50° C.–68° C. being established. It is optionally possible to lower the salt concentration to 0.1× SSC. Polynucleotide fragments which are, for example, at least 70% or at least 80% or at least 90% to 95% identical to the sequence of the probe employed can be isolated by increasing the hybridization temperature stepwise from 50° C. to 68° C. in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984) I.B.R. and in Newton and Graham: PCR (Spektrum Akademischer Verlag, Heidelberg, Germany, 1994) I.B.R.

It has been found that coryneform bacteria produce amino acids in an improved manner after attenuation of the gorA gene.

To achieve an attenuation, either the expression of the gorA gene or the catalytic properties of the enzyme protein can be reduced or eliminated. The two measures can optionally be combined.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246 I.B.R., in Boyd and Murphy (Journal of Bacteriology 170: 5949 (1988)) I.B.R., in Voskuil and Chambliss (Nucleic Acids Research 26: 3548 (1998) I.B.R., in Jensen and Hammer (Biotechnology and Bioengineering 58: 191 (1998)) I.B.R., in Pátek et al. (Microbiology 142: 1297 (1996)) I.B.R., Vasicova et al. (Journal of Bacteriology 181: 6188 (1999)) I.B.R. and in known textbooks of genetics and molecular biology, such as e.g. the textbook by Knippers ("Molekulare Genetik [Molecular Genetics]", 6th edition, Georg Thieme Verlag, Stuttgart, Germany, 1995) I.B.R. or that by Winnacker ("Gene und Klone [Genes and Clones]", VCH Verlagsgesellschaft, Weinheim, Germany, 1990) I.B.R.

Mutations which lead to a change or reduction in the catalytic properties of enzyme proteins are known from the prior art; examples which may be mentioned are the works by Qiu and Goodman (Journal of Biological Chemistry 272: 8611–8617 (1997)) I.B.R., Sugimoto et al. (Bioscience Biotechnology and Biochemistry 61: 1760–1762 (1997)) I.B.R. and Möckel ("Die Threonindehydratase aus Corynebacterium glutamicum: Aufhebung der allosterischen Regulation und Struktur des Enzyms", Reports from the Jülich Research Center, Jül-2906, ISSN09442952, Jülich, Germany, 1994) I.B.R. Summarizing descriptions can be found in known textbooks of genetics and molecular biology, such as e.g. that by Hagemann ("Allgemeine Genetik", Gustav Fischer Verlag, Stuttgart, 1986) I.B.R.

Possible mutations are transitions, transversions, insertions and deletions. Depending on the effect of the amino acid exchange on the enzyme activity, "missense mutations" or "nonsense mutations" are referred to. Insertions or deletions of at least one base pair (bp) in a gene lead to frame shift mutations, as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik", 6th edition, Georg Thieme Verlag, Stuttgart, Germany, 1995) I.B.R., that by Winnacker ("Gene und Klone", VCH Verlagsgesellschaft, Weinheim, Germany, 1990) or that by Hagemann ("Allgemeine Genetik", Gustav Fischer Verlag, Stuttgart, 1986) I.B.R.

A common method of mutating genes of C. glutamicum is the method of "gene disruption" and "gene replacement" described by Schwarzer and Pühler (Bio/Technology 9, 84–87 (1991)) I.B.R.

In the method of gene disruption a central part of the coding region of the gene of interest is cloned in a plasmid vector which can replicate in a host (typically *E. coli*), but not in *C. glutamicum*. Possible vectors are, for example, pSUP301 (Simon et al., Bio/Technology 1, 784–791 (1983) I.B.R.), pK18mob or pK19mob (Schäfer et al., Gene 145, 69–73 (1994) I.B.R.), pK18mobsacB or pK19mobsacB (Jäger et al., Journal of Bacteriology 174: 5462–65 (1992) I.B.R.), pGEM-T (Promega corporation, Madison, Wis., USA), pCR2.1-TOPO (Shuman (1994). Journal of Biological Chemistry 269:32678–84 I.B.R.; U.S. Pat. No. 5,487,993 I.B.R.), pCR®Blunt (Invitrogen, Groningen, Holland; Bernard et al., Journal of Molecular Biology, 234: 534–541 (1993) I.B.R.) or pEM1 (Schrumpf et al, 1991, Journal of Bacteriology 173:4510–4516 I.B.R.). The plasmid vector which contains the central part of the coding region of the gene is then transferred into the desired strain of *C. glutamicum* by conjugation or transformation. The method of conjugation is described, for example, by Schäfer et al. (Applied and Environmental Microbiology 60, 756–759 (1994)) I.B.R. Methods for transformation are described, for example, by Thierbach et al. (Applied Microbiology and Biotechnology 29, 356–362 (1988)) I.B.R., Dunican and Shivnan (Bio/Technology 7, 1067–1070 (1989) I.B.R.) and Tauch et al. (FEMS Microbiological Letters 123, 343–347 (1994)) I.B.R. After homologous recombination by means of a "cross-over" event, the coding region of the gene in question is interrupted by the vector sequence and two incomplete alleles are obtained, one lacking the 3' end and one lacking the 5' end. This method has been used, for example, by Fitzpatrick et al. (Applied Microbiology and Biotechnology 42, 575–580 (1994)) I.B.R. to eliminate the recA gene of *C. glutamicum*.

In the method of "gene replacement", a mutation, such as e.g. a deletion, insertion or base exchange, is established in vitro in the gene of interest. The allele prepared is in turn cloned in a vector which is not replicative for *C. glutamicum* and this is then transferred into the desired host of *C. glutamicum* by transformation or conjugation. After homologous recombination by means of a first "cross-over" event which effects integration and a suitable second "cross-over" event which effects excision in the target gene or in the target sequence, the incorporation of the mutation or of the allele is achieved. This method was used, for example, by Peters-Wendisch et al. (Microbiology 144, 915–927 (1998)) I.B.R. to eliminate the pyc gene of *C. glutamicum* by a deletion.

A deletion, insertion or a base exchange can be incorporated into the gorA gene in this manner.

In addition, it may be advantageous for the production of L-amino acids to enhance, in particular over-express, one or more enzymes of the particular biosynthesis pathway, of glycolysis, of anaplerosis, of the citric acid cycle, of the pentose phosphate cycle, of amino acid export and optionally regulatory proteins, in addition to the attenuation of the gorA gene.

The term "enhancement" in this connection describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

Thus, for the preparation of L-amino acids, in addition to the attenuation of the gorA gene, at the same time one or more of the genes chosen from the group consisting of the dapA gene which codes for dihydrodipicolinate synthase (EP-B 0 197 335 I.B.R.), the gap gene which codes for glyceraldehyde 3-phosphate dehydrogenase (Eikmanns (1992), Journal of Bacteriology 174:6076–6086 I.B.R.), the tpi gene which codes for triose phosphate isomerase (Eikmanns (1992), Journal of Bacteriology 174:6076–6086 the pgk gene which codes for 3-phosphoglycerate kinase (Eikmanns (1992), Journal of Bacteriology 174:6076–6086 I.B.R.), the zwf gene which codes for glucose 6-phosphate dehydrogenase (JP-A-09224661 I.B.R.), the pyc gene which codes for pyruvate carboxylase (DE-A-198 31 609 I.B.R.), the mqo gene which codes for malate-quinone oxidoreductase (Molenaar et al., European Journal of Biochemistry 254, 395–403 (1998) I.B.R.), the lysC gene which codes for a feed-back resistant aspartate kinase (EP-B-0387527 I.B.R.; EP-A-0699759 I.B.R.; WO 00/63388 I.B.R.), the lysE gene which codes for lysine export (DE-A-195 48 222 I.B.R.), the hom gene which codes for homoserine dehydrogenase (EP-A 0131171 I.B.R.), the ilvA gene which codes for threonine dehydratase (Möckel et al., Journal of Bacteriology (1992) 8065–8072) I.B.R.) or the ilvA(Fbr) allele which codes for a "feed back resistant" threonine dehydratase (Möckel et al., (1994) Molecular Microbiology 13: 833–842 I.B.R.), the ilvBN gene which codes for acetohydroxy-acid synthase (EP-B 0356739 I.B.R.), the ilvD gene which codes for dihydroxy-acid dehydratase (Sahm and Eggeling (1999) Applied and Environmental Microbiology 65: 1973–1979 I.B.R.), the zwa1 gene which codes for the Zwa1 protein (DE: 19959328.0 I.B.R., DSM 13115)

can be enhanced, in particular over-expressed.

It may furthermore be advantageous for the production of amino acids, in addition to the attenuation of the gorA gene, at the same time for one or more of the genes chosen from the group consisting of the pck gene which codes for phosphoenol pyruvate carboxykinase (DE 199 50 409.1 I.B.R. DSM 13047), the pgi gene which codes for glucose 6-phosphate isomerase (U.S. Ser. No. 09/396,478 I.B.R., DSM 12969), the poxB gene which codes for pyruvate oxidase (DE:1995 1975.7 I.B.R., DSM 13114), the zwa2 gene which codes for the Zwa2 protein (DE: 19959327.2 I.B.R., DSM 13113)

to be attenuated, in particular for the expression thereof to be reduced.

In addition to the attenuation of the gorA gene it may furthermore be advantageous for the production of amino acids to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982 I.B.R.).

The invention also provides the microorganisms prepared according to the invention, and these can be cultured continuously or discontinuously in the batch process (batch culture) or in the fed batch (feed process) or repeated fed batch process (repetitive feed process) for the purpose of production of L-amino acids. A summary of known culture methods is described in the textbook by Chmiel (Bioprozesstechnik 1. Einführung in die Bioverfahrenstechnik (Gustav Fischer Verlag, Stuttgart, 1991) I.B.R.) or in the textbook by Storhas (Bioreaktoren und periphere Einrichtungen (Vieweg Verlag, Braunschweig/Wiesbaden, 1994) I.B.R.).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981) I.B.R.

Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) I.B.R. by anion exchange chromatography with subsequent ninhydrin derivation, or it can be carried out by reversed phase HPLC, for example as described by Lindroth et al. (Analytical Chemistry (1979) 51: 1167–1174) I.B.R.

The process according to the invention is used for fermentative preparation of amino acids.

The following microorganism was deposited on 12.01.2001 as a pure culture at the Deutsche Sammlung für Mikroorganismen und Zellkulturen (DSMZ=German Collection of Microorganisms and Cell Cultures, Braunschweig, Germany) in accordance with the Budapest Treaty:

Escherichia coli Top10/pCR2.1gorAint as DSM 13983.

The present invention is explained in more detail in the following with the aid of embodiment examples.

The isolation of plasmid DNA from Escherichia coli and all techniques of restriction, Klenow and alkaline phosphatase treatment were carried out by the method of Sambrook et al. (Molecular Cloning. A Laboratory Manual, 1989, Cold Spring Harbour Laboratory Press, Cold Spring Harbor, N.Y., USA) I.B.R. Methods for transformation of Escherichia coli are also described in this handbook.

The composition of the usual nutrient media, such as LB or TY medium, can also be found in the handbook by Sambrook et al. I.B.R.

EXAMPLE 1

Preparation of a Genomic Cosmid Gene Library from C. glutamicum ATCC 13032

Chromosomal DNA from C. glutamicum ATCC 13032 was isolated as described by Tauch et al. (1995, Plasmid 33:168–179) I.B.R. and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987), Proceedings of the National Academy of Sciences, USA 84:2160–2164 I.B.R.), obtained from Stratagene (La Jolla, USA, Product Description SuperCos1 Cosmid Vector Kit, Code no. 251301 I.B.R.) was cleaved with the restriction enzyme XbaI (Amersham Pharmacia, Freiburg, Germany, Product Description XbaI, Code no. 27-0948-02 I.B.R.) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04 I.B.R.). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04 I.B.R.). The ligation mixture was then packed in phages with the aid of Gigapack II XL Packing Extract (Stratagene, La Jolla, USA, Product Description Gigapack II XL Packing Extract, Code no. 200217 I.B.R.).

For infection of the E. coli strain NM554 (Raleigh et al. 1988, Nucleic Acid Res. 16:1563–1575 I.B.R.) the cells were taken up in 10 mM $MgSO_4$ and mixed with an aliquot of the phage suspension. The infection and titering of the cosmid library were carried out as described by Sambrook et al. (1989, Molecular Cloning: A Laboratory Manual, Cold Spring Harbor I.B.R.), the cells being plated out on LB agar (Lennox, 1955, Virology, 1:190 I.B.R.)+100 µg/ml ampicillin. After incubation overnight at 37° C., recombinant individual clones were selected.

EXAMPLE 2
Isolation and Sequencing of the gorA Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02 I.B.R.). The DNA fragments were dephosphorylated with shrimp alkaline phosphatase (Roche Molecular Biochemicals, Mannheim, Germany, Product Description SAP, Product No. 1758250 I.B.R.). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01 I.B.R.) was cleaved with the restriction enzyme BamHI (Amersham Pharmacia, Freiburg, Germany, Product Description BamHI, Product No. 27-0868-04 I.B.R.). The ligation of the cosmid fragments in the sequencing vector pZero-1 was carried out as described by Sambrook et al. (1989, Molecular Cloning: A Laboratory Manual, Cold Spring Harbor I.B.R.), the DNA mixture being incubated overnight with T4 ligase (Pharmacia Biotech, Freiburg, Germany). This ligation mixture was then electroporated (Tauch et al. 1994, FEMS Microbiol. Letters, 123:343-7 I.B.R.) into the *E. coli* strain DH5αmcr (Grant, 1990, Proceedings of the National Academy of Sciences, U.S.A., 87:4645-4649 I.B.R.). Letters, 123:343-7 I.B.R.) and plated out on LB agar (Lennox, 1955, Virology, 1:190 I.B.R.) with 50 pg/ml zeocin.

The plasmid preparation of the recombinant clones was carried out with the Biorobot 9600 (Product No. 900200, Qiagen, Hilden, Germany). The sequencing was carried out by the dideoxy chain termination method of Sanger et al. (1977, Proceedings of the National Academies of Sciences, U.S.A., 74:5463-5467 I.B.R.) with modifications according to Zimmermann et al. (1990, Nucleic Acids Research, 18:1067) I.B.R. The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217-231 I.B.R.) version 97-0. The individual sequences of the pZero1 derivatives were assembled to a continuous contig. The computer-assisted coding region analyses were prepared with the XNIP program (Staden, 1986, Nucleic Acids Research, 14:217-231 I.B.R.). Further analyses were carried out with the "BLAST search program" (Altschul et al., 1997, Nucleic Acids Research, 25:3389-3402 I.B.R.) against the non-redundant databank of the "National Center for Biotechnology Information" (NCBI, Bethesda, Md., USA) I.B.R.

The relative degree of substitution or mutation in the polynucleotide or amino acid sequence to produce a desired percentage of sequence identity can be established or determined by well-known methods of sequence analysis. These methods are disclosed and demonstrated in Bishop, et al. "DNA & Protein Sequence Analysis (A Practical Approach"), Oxford Univ. Press, Inc. (1997) I.B.R. and by Steinberg, Michael "Protein Structure Prediction" (A Practical Approach), Oxford Univ. Press, Inc. (1997) I.B.R.

The resulting nucleotide sequence is shown in SEQ ID No. 1. Analysis of the nucleotide sequence showed an open reading frame of 1398 bp, which was called the gorA gene. The gorA gene codes for a polypeptide of 465 amino acids.

EXAMPLE 3
Preparation of an Integration Vector for Integration Mutagenesis of the gorA Gene From the strain ATCC 13032, chromosomal DNA was isolated by the method of Eikmanns et al. (Microbiology 140: 1817-1828 (1994) I.B.R.). On the basis of the sequence of the gorA gene known for *C. glutamicum* from example 2, the following oligonucleotides were chosen for the polymerase chain reaction (see SEQ ID No. 3 and SEQ ID No. 4):

```
gorA-int1:
5' ACC AAC GAA GAC ATC ATG C 3'    SEQ ID NO:3 gorA-int2:
5' ATC ATG TGG CAT CTT CTG C 3'    SEQ ID NO:4
```

The primers shown were synthesized by MWG Biotech (Ebersberg, Germany) and the PCR reaction was carried out by the standard PCR method of Innis et al. (PCR protocols. A guide to methods and applications, 1990, Academic Press I.B.R.) with the Taq-polymerase from Boehringer Mannheim (Germany, Product Description Taq DNA polymerase, Product No. 1 146 165 I.B.R.). With the aid of the polymerase chain reaction, the primers allow amplification of an internal fragment of the gorA gene 540 bp in size. The product amplified in this way was tested electrophoretically in a 0.8% agarose gel.

The amplified DNA fragment was ligated with the TOPO TA Cloning Kit from Invitrogen Corporation (Carlsbad, Calif., USA; Catalogue Number K4500-01) in the vector pCR2.1-TOPO (Mead at al. (1991) Bio/Technology 9:657-663 I.B.R.).

Figure 1:
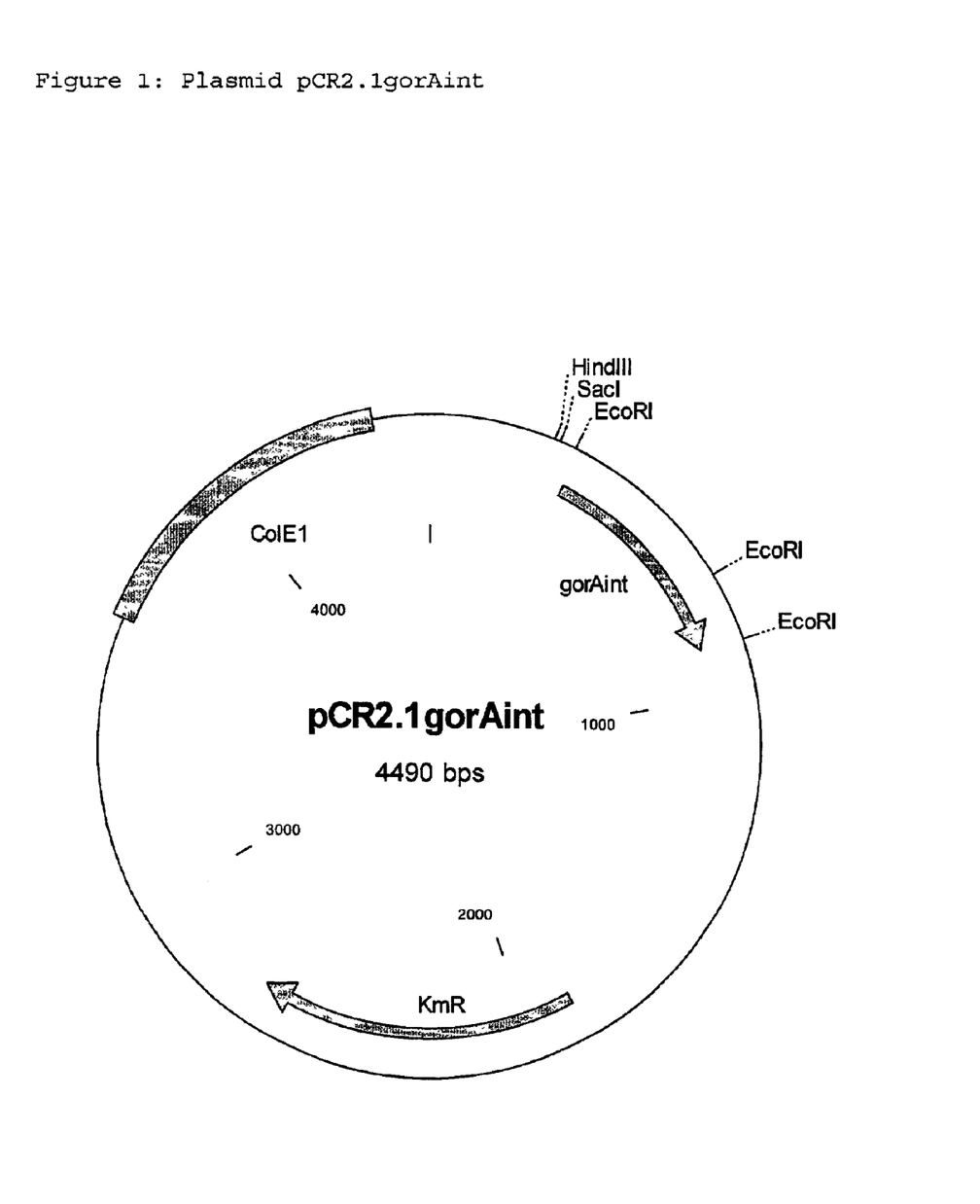
FIG. 1: Map of the plasmid pCR2.1gorAint.

The *E. coli* strain TOP10 was then electroporated with the ligation batch (Hanahan, In: DNA Cloning. A Practical Approach. Vol. I, IRL-Press, Oxford, Washington D.C., USA, 1985 I.B.R.). Selection of plasmid-carrying cells was carried out by plating out the transformation batch on LB Agar (Sambrook et al., Molecular cloning: a laboratory manual. 2$^{nd}$ Ed. Cold Spring Harbor Laboratory Press, Cold Spring Harbor, N.Y., 1989 I.B.R.), which had been supplemented with 50 mg/l kanamycin. Plasmid DNA was isolated from a transformant with the aid of the QIAprep Spin Miniprep Kit from Qiagen and checked by restriction with the restriction enzyme EcoRI and subsequent agarose gel electrophoresis (0.8%). The plasmid was called pCR2.1gorAint and is shown in FIG. 1.

EXAMPLE 4
Integration Mutagenesis of the gorA Gene in the Strain DSM 5715

The vector pCR2.1gorAint mentioned in example 3 was electroporated by the electroporation method of Tauch et al.(FEMS Microbiological Letters, 123:343-347 (1994)) I.B.R. in *Corynebacterium glutamicum* DSM 5715. The strain DSM 5715 is an AEC-resistant lysine producer. The vector pCR2.1gorAint cannot replicate independently in DSM5715 and is retained in the cell only if it has integrated into the chromosome of DSM 5715. Selection of clones with pCR2.1gorAint integrated into the chromosome was carried out by plating out the electroporation batch on LB agar (Sambrook et al., Molecular cloning: a laboratory manual. 2nd Ed. Cold Spring Harbor Laboratory Press, Cold Spring Harbor, N.Y. I.B.R.), which had been supplemented with 15 mg/l kanamycin.

For detection of the integration, the gorAint fragment was labeled with the Dig hybridization kit from Boehringer by the method of "The DIG System Users Guide for Filter Hybridization" of Boehringer Mannheim GmbH (Mannheim, Germany, 1993) I.B.R. Chromosomal DNA of a potential integrant was isolated by the method of Eikmanns et al. (Microbiology 140: 1817–1828 (1994)) I.B.R. and in each case cleaved with the restriction enzymes SacI, EcoRI and HindIII. The fragments formed were separated by means of agarose gel electrophoresis and hybridized at 68° C. with the Dig hybridization kit from Boehringer. The plasmid pCR2.1gorAint mentioned in example 3 had been inserted into the chromosome of DSM5715 within the chromosomal gorA gene. The strain was called DSM5715::pCR2.1gorAint.

EXAMPLE 5

Preparation of Lysine

The *C. glutamicum* strain DSM5715::pCR2.1gorAint obtained in example 4 was cultured in a nutrient medium suitable for the production of lysine and the lysine content in the culture supernatant was determined.

For this, the strain was first incubated on an agar plate with the corresponding antibiotic (brain-heart agar with kanamycin (25 mg/l)) for 24 hours at 33° C. Starting from this agar plate culture, a preculture was seeded (10 ml medium in a 100 ml conical flask). The complete medium CgIII was used as the medium for the preculture.

| [0088] | Medium Cg III |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamycin (25 mg/l) was added to this. The preculture was incubated for 16 hours at 33° C. at 240 rpm on a shaking machine. A main culture was seeded from this preculture such that the initial OD (660 nm) of the main culture was 0.1 OD. Medium MM was used for the main culture.

| [0089] | Medium MM |
|---|---|
| CSL (corn steep liquor) | 5 g/l |
| MOPS | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| Leucine (sterile-filtered) | 0.1 g/l |
| $CaCO_3$ | 25 g/l |

The CSL, MOPS and the salt solution are brought to pH 7 with aqueous ammonia and autoclaved. The sterile substrate and vitamin solutions are then added, and the $CaCO_3$ autoclaved in the dry state is added.

Culturing is carried out in a 10 ml volume in a 100 ml conical flask with baffles. Kanamycin (25 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivation with ninhydrin detection.

The result of the experiment is shown in table 1.

TABLE 1

| Strain | OD (660 nm) | Lysine HCl g/l |
|---|---|---|
| DSM5715 | 8.2 | 13.74 |
| DSM5715::pCR2.1gorAint | 8.5 | 14.65 |

This application claims priority to German Priority Document Application No. 100 44 946.8, filed on Sep. 12, 2000 and to German Priority Document Application No. 101 09 023.4, filed on Feb. 24, 2001. Both German Priority Documents are hereby incorporated by reference in their entirety.

We claim:

1. An isolated polynucleotide, comprising the nucleic acid sequence as shown in SEQ ID NO: 1.

2. An isolated polynucleotide, comprising a polynucleotide sequence which encodes a polypeptide having the amino acid sequence of SEQ ID NO: 2.

3. An integration vector in *E. coli* strain Top10/pCR2.1gorAint deposited as DSM 13983.

4. An isolated fragment of the gorA gene consisting of at least 540 nucleotides or consisting of at least 15 successive nucleotides of SEQ ID NO: 1.

5. A recombinant coryneform bacteria in which the gorA gene is eliminated, wherein said gorA gene consists of a nucleotide sequence that encodes a polypeptide having the enzymatic activity of a glutathione reductase and comprising the amino acid sequence of SEQ ID NO:2.

6. A recombinant coryneform bacterium, comprising a vector which comprises a polynucleotide consisting of at least 15 successive nucleotides of the polynucleotide of claim 1, wherein said vector is integrated into the gorA gene of said coryneform bacterium consisting of a nucleotide sequence that encodes a polypeptide comprising the amino acid sequence of SEQ ID NO: 2 thereby eliminating said polypeptide.

7. The isolated polynucleotide according to claim 1, wherein said polynucleotide is native to *Corynebacterium glutamicum*.

8. An isolated polynucleotide comprising a complete complement of the polynucleotide of claim 1.

9. An isolated polynucleotide which hybridizes under stringent conditions to the complete complement of SEQ ID NO: 1, wherein said stringent conditions comprise washing in 0.5×SSC at a temperature of 68° C., and wherein the polynucleotide encodes a protein having glutathione reductase activity.

10. An isolated polynucleotide consisting of SEQ ID NO: 1 or a fragment thereof which encodes a protein consisting of the amino acid sequence of SEQ ID NO: 2.

11. An isolated polynucleotide comprising nucleotides 250 to 1644 of SEQ ID NO: 1, wherein said isolated polynucleotide encodes a polypeptide having glutathionine reductase activity.

12. An isolated polynucleotide consisting of at least 15 consecutive nucleotides selected from SEQ ID NO: 1 or a complete complement of SEQ ID NO: 1.

13. The isolated polynucleotide according to claim 12, wherein the polynucleotide is a primer or a probe.

14. A recombinant coryneform bacterium, wherein, in said bacterium, a polypeptide having glutathione reductase enzymatic activity and encoded by the polynucleotide of SEQ ID NO: 1 is eliminated due to mutagenesis of said polynucleotide, wherein said mutagenesis comprises one or more methods selected from the group consisting of deletion mutagenesis of two or more codons, insertion, and deletion mutagenesis of at least one nucleotide and transition or transversion mutagenesis of at least one nucleotide with incorporation of a nonsense mutation.

15. A recombinant coryneform bacterium, wherein, in said bacterium, a polypeptide comprising the amino acid sequence of SEQ ID NO:2 and having glutathione reductase enzymatic activity is eliminated due to mutagenesis of a polynucleotide encoding said polypeptide selected from the group consisting of deletion mutagenesis of two or more codons, insertion or deletion mutagenesis of at least one nucleotide and transition, and transversion mutagenesis of at least one nucleotide with incorporation of a nonsense mutation.

16. A recombinant coryneform bacterium, wherein, in said bacterium, a polypeptide having glutathione reductase enzymatic activity and encoded by a polynucleotide that hybridizes under stringent conditions to a complete complement of SEQ ID NO:1, wherein said stringent conditions comprise washing in 0.5×SSC at a temperature of 68° C., is eliminated due to mutagenesis of said polynucleotide, wherein said mutagenesis comprises one or more methods selected from the group consisting of deletion mutagenesis of two or more codons, insertion or deletion mutagenesis of at least one nucleotide and transition, and transversion mutagenesis of at least one nucleotide with incorporation of a nonsense mutation.

17. The coryneform bacterium of any of the claims 14–16 wherein said mutagenesis comprises insertion of at least one nucleotide into said polynucleotide.

18. The coryneform bacterium of any of the claims 14–16 wherein said bacterium is transformed with plasmid pCR2.1gorAint deposited under DSM 13983.

* * * * *

SEQUENCE LISTING

<160> NUMBER OF SEQ ID NOS: 4

<210> SEQ ID NO 1
<211> LENGTH: 1880
<212> TYPE: DNA
<213> ORGANISM: Corynebacterium glutamicum
<220> FEATURE:
<221> NAME/KEY: CDS
<222> LOCATION: (250)..(1644)
<223> OTHER INFORMATION:

<400> SEQUENCE: 1
aacgctcgcc acgatatttt cctctcaagg aaacccgcca gagatcacgc ctctgaagta      60
ctcaacaact ggctgcaatc gaagctttcc agcctcaaac catctcaata acaccgcgaa     120

```
ttatagactg aactggtact tgggaagctt tttatagtca tatgcgttga gatacgtgga        180
cgacaaagca ccagttagtt gccttcccag tccagcccac atccgatttc taaattagga        240 gcacatctt atg tct gag cag cca gct tcc att aag cat tat gac ctc atc        291
          Met Ser Glu Gln Pro Ala Ser Ile Lys His Tyr Asp Leu Ile
          1               5                   10 atc att ggt acc ggc tct gga aac tcc att cct gga cca gag ttt gat        339
Ile Ile Gly Thr Gly Ser Gly Asn Ser Ile Pro Gly Pro Glu Phe Asp
15              20                  25                  30 gat aaa tca att gcc atc gtg gaa aag ggt gct ttc ggc gga act tgc        387
Asp Lys Ser Ile Ala Ile Val Glu Lys Gly Ala Phe Gly Gly Thr Cys
            35                  40                  45 ctc aat gtg ggc tgc atc cct acc aag atg tac gtt tac gct gcg gat        435
Leu Asn Val Gly Cys Ile Pro Thr Lys Met Tyr Val Tyr Ala Ala Asp
        50                  55                  60 atc gct caa gaa att cag gag tct gct cgc ctg ggt atc gat gcg acg        483
Ile Ala Gln Glu Ile Gln Glu Ser Ala Arg Leu Gly Ile Asp Ala Thr
    65                  70                  75 gtc aac agc gtg gat tgg cct tcc atc gtc agc cgc gtt ttc gac aag        531
Val Asn Ser Val Asp Trp Pro Ser Ile Val Ser Arg Val Phe Asp Lys
80                  85                  90 cgc atc gac ctc atc gcg caa ggc ggc gag gct tat cga cgt ggc ccc        579
Arg Ile Asp Leu Ile Ala Gln Gly Gly Glu Ala Tyr Arg Arg Gly Pro
95              100                 105                 110 gaa act cca aac atc gat gtg tat gac atg cac gca tcg ttt gtt gat        627
Glu Thr Pro Asn Ile Asp Val Tyr Asp Met His Ala Ser Phe Val Asp
            115                 120                 125 tcc aag aca atc tcc act ggt att gcc ggc caa gaa cag ctg atc agc        675
Ser Lys Thr Ile Ser Thr Gly Ile Ala Gly Gln Glu Gln Leu Ile Ser
        130                 135                 140 ggt act gac att gta atc gca acc ggc tcc cgc cct tac atc cct gaa        723
Gly Thr Asp Ile Val Ile Ala Thr Gly Ser Arg Pro Tyr Ile Pro Glu
    145                 150                 155 gct att gca gag tcc ggc gca cgc tac tac acc aac gaa gac atc atg        771
Ala Ile Ala Glu Ser Gly Ala Arg Tyr Tyr Thr Asn Glu Asp Ile Met
160                 165                 170 cgc ctg gca cag cag cct gaa tct ttg gtg att gtt ggt ggc ggt ttc        819
Arg Leu Ala Gln Gln Pro Glu Ser Leu Val Ile Val Gly Gly Gly Phe
175                 180                 185                 190 atc gct ttg gaa ttt gct cac gtt ttt gaa gcg ctt ggc acc aag gtc        867
Ile Ala Leu Glu Phe Ala His Val Phe Glu Ala Leu Gly Thr Lys Val
            195                 200                 205 acc atc ctc aac cgc tct gac gtg ctg ctg cgc gag gca gat gca gac        915
Thr Ile Leu Asn Arg Ser Asp Val Leu Leu Arg Glu Ala Asp Ala Asp
        210                 215                 220 atc tcc gcg aaa atc ctc gag ctt tcc aaa aag cgt ttc gac gtc cgc        963
Ile Ser Ala Lys Ile Leu Glu Leu Ser Lys Lys Arg Phe Asp Val Arg
    225                 230                 235 ctc agc act gcg gtc acc gca gta cac aac aag gcc gac ggc ggc gtg       1011
Leu Ser Thr Ala Val Thr Ala Val His Asn Lys Ala Asp Gly Gly Val
240                 245                 250 aag atc tcc acc gac acc ggc gac gac atc gag gca gat att ttg ctc       1059
Lys Ile Ser Thr Asp Thr Gly Asp Asp Ile Glu Ala Asp Ile Leu Leu
255                 260                 265                 270 gtt gcc act ggt cgc acc cct aac ggc aac caa atg aac ttg gac gcc       1107
Val Ala Thr Gly Arg Thr Pro Asn Gly Asn Gln Met Asn Leu Asp Ala
            275                 280                 285 gca ggc atc gag atg aac ggt cgt tcc atc aag gtt gat gaa ttc ggt       1155
Ala Gly Ile Glu Met Asn Gly Arg Ser Ile Lys Val Asp Glu Phe Gly
```

-continued

```
                   290                 295                 300
cgc acc agt gtt gaa ggc gtg tgg gcg ctt ggc gat gtc tcc tcc cct    1203
Arg Thr Ser Val Glu Gly Val Trp Ala Leu Gly Asp Val Ser Ser Pro
        305                 310                 315 tac aag ctc aag cac gta gcc aat gcg gaa atg cga gca atc aag cac    1251
Tyr Lys Leu Lys His Val Ala Asn Ala Glu Met Arg Ala Ile Lys His
        320                 325                 330 aac ctt gcc aac cct aat gac ctg cag aag atg cca cat gat ttc gtg    1299
Asn Leu Ala Asn Pro Asn Asp Leu Gln Lys Met Pro His Asp Phe Val
335                 340                 345                 350 cca tca gct gtt ttc acc aac cct cag atc tcg cag gtc ggc atg act    1347
Pro Ser Ala Val Phe Thr Asn Pro Gln Ile Ser Gln Val Gly Met Thr
                355                 360                 365 gag cag gag gcg cgt gaa gct ggc ctc gac atc act gtg aag atc cag    1395
Glu Gln Glu Ala Arg Glu Ala Gly Leu Asp Ile Thr Val Lys Ile Gln
                370                 375                 380 aac tac tct gat gtg gct tat ggc tgg gcc atg gaa gat aag gat gga    1443
Asn Tyr Ser Asp Val Ala Tyr Gly Trp Ala Met Glu Asp Lys Asp Gly
385                 390                 395 ttc gtt aag ctc att gcc gat aag gac acc ggc aag ttg gtc ggc gcg    1491
Phe Val Lys Leu Ile Ala Asp Lys Asp Thr Gly Lys Leu Val Gly Ala
        400                 405                 410 cac atc att ggt gct caa gcc tca aca ctg atc cag caa ctg atc act    1539
His Ile Ile Gly Ala Gln Ala Ser Thr Leu Ile Gln Gln Leu Ile Thr
415                 420                 425                 430 gtc atg gca ttt gga atc gat gca cga gaa gct gca acc aag cag tac    1587
Val Met Ala Phe Gly Ile Asp Ala Arg Glu Ala Ala Thr Lys Gln Tyr
                435                 440                 445 tgg att cac cct gct ctt cca gaa gtc atc gaa aac gct ctt ctg ggg    1635
Trp Ile His Pro Ala Leu Pro Glu Val Ile Glu Asn Ala Leu Leu Gly
                450                 455                 460 cta gag ttt tagaagctta cgcagccgta agttttgagt atcgaaaaat            1684
Leu Glu Phe
        465 ttccacgtca agttaactgc gttaataaag gtggagaata agttgttttcc aagatcaatt    1744 caaggaaagt tgcattttcg caggtcagtg ttacccccta agactacccc tttccattgc    1804 atacaaagga aatacatata gacttttggg cattagatta cctcgataaa agtttaggga    1864 atctaaattc attgat                                                   1880

<210> SEQ ID NO 2
<211> LENGTH: 465
<212> TYPE: PRT
<213> ORGANISM: Corynebacterium glutamicum

<400> SEQUENCE: 2

Met Ser Glu Gln Pro Ala Ser Ile Lys His Tyr Asp Leu Ile Ile
1               5                   10                  15

Gly Thr Gly Ser Gly Asn Ser Ile Pro Gly Pro Glu Phe Asp Asp Lys
                20                  25                  30

Ser Ile Ala Ile Val Glu Lys Gly Ala Phe Gly Gly Thr Cys Leu Asn
            35                  40                  45

Val Gly Cys Ile Pro Thr Lys Met Tyr Val Tyr Ala Ala Asp Ile Ala
        50                  55                  60

Gln Glu Ile Gln Glu Ser Ala Arg Leu Gly Ile Asp Ala Thr Val Asn
65                  70                  75                  80

Ser Val Asp Trp Pro Ser Ile Val Ser Arg Val Phe Asp Lys Arg Ile
                85                  90                  95
```

```
Asp Leu Ile Ala Gln Gly Gly Glu Ala Tyr Arg Arg Gly Pro Glu Thr
            100                 105                 110
Pro Asn Ile Asp Val Tyr Asp Met His Ala Ser Phe Val Asp Ser Lys
            115                 120                 125
Thr Ile Ser Thr Gly Ile Ala Gly Gln Glu Gln Leu Ile Ser Gly Thr
            130                 135                 140
Asp Ile Val Ile Ala Thr Gly Ser Arg Pro Tyr Ile Pro Glu Ala Ile
145                 150                 155                 160
Ala Glu Ser Gly Ala Arg Tyr Tyr Thr Asn Glu Asp Ile Met Arg Leu
                165                 170                 175
Ala Gln Gln Pro Glu Ser Leu Val Ile Val Gly Gly Phe Ile Ala
                180                 185                 190
Leu Glu Phe Ala His Val Phe Glu Ala Leu Gly Thr Lys Val Thr Ile
            195                 200                 205
Leu Asn Arg Ser Asp Val Leu Leu Arg Glu Ala Asp Ala Asp Ile Ser
            210                 215                 220
Ala Lys Ile Leu Glu Leu Ser Lys Lys Arg Phe Asp Val Arg Leu Ser
225                 230                 235                 240
Thr Ala Val Thr Ala Val His Asn Lys Ala Asp Gly Val Lys Ile
                245                 250                 255
Ser Thr Asp Thr Gly Asp Asp Ile Glu Ala Asp Ile Leu Leu Val Ala
            260                 265                 270
Thr Gly Arg Thr Pro Asn Gly Asn Gln Met Asn Leu Asp Ala Ala Gly
            275                 280                 285
Ile Glu Met Asn Gly Arg Ser Ile Lys Val Asp Glu Phe Gly Arg Thr
            290                 295                 300
Ser Val Glu Gly Val Trp Ala Leu Gly Asp Val Ser Ser Pro Tyr Lys
305                 310                 315                 320
Leu Lys His Val Ala Asn Ala Glu Met Arg Ala Ile Lys His Asn Leu
                325                 330                 335
Ala Asn Pro Asn Asp Leu Gln Lys Met Pro His Asp Phe Val Pro Ser
            340                 345                 350
Ala Val Phe Thr Asn Pro Gln Ile Ser Gln Val Gly Met Thr Glu Gln
            355                 360                 365
Glu Ala Arg Glu Ala Gly Leu Asp Ile Thr Val Lys Ile Gln Asn Tyr
            370                 375                 380
Ser Asp Val Ala Tyr Gly Trp Ala Met Glu Asp Lys Asp Gly Phe Val
385                 390                 395                 400
Lys Leu Ile Ala Asp Lys Asp Thr Gly Lys Leu Val Gly Ala His Ile
                405                 410                 415
Ile Gly Ala Gln Ala Ser Thr Leu Ile Gln Gln Leu Ile Thr Val Met
            420                 425                 430
Ala Phe Gly Ile Asp Ala Arg Glu Ala Thr Lys Gln Tyr Trp Ile
            435                 440                 445
His Pro Ala Leu Pro Glu Val Ile Glu Asn Ala Leu Leu Gly Leu Glu
    450                 455                 460
Phe
465

<210> SEQ ID NO 3
<211> LENGTH: 19
<212> TYPE: DNA
<213> ORGANISM: Corynebacterium glutamicum
```

-continued

```
<400> SEQUENCE: 3
accaacgaag acatcatgc                                              19

<210> SEQ ID NO 4
<211> LENGTH: 19
<212> TYPE: DNA
<213> ORGANISM: Corynebacterium glutamicum

<400> SEQUENCE: 4
atcatgtggc atcttctgc                                              19
```